(12) United States Patent
Wettendorff

(10) Patent No.: US 7,101,560 B2
(45) Date of Patent: Sep. 5, 2006

(54) COMBINATION VACCINE FOR ADMINISTRATION TO ADOLESCENTS

(75) Inventor: Martine Anne Cecile Wettendorff, Rixensart (BE)

(73) Assignee: SmithKline Beecham Biologicals s.a., Rixensart (BE)

(*) Notice: Subject to any disclaimer, the term of this patent is extended or adjusted under 35 U.S.C. 154(b) by 0 days.

(21) Appl. No.: 10/734,857

(22) Filed: Dec. 12, 2003

(65) Prior Publication Data

US 2004/0126394 A1 Jul. 1, 2004

Related U.S. Application Data

(62) Division of application No. 10/070,479, filed as application No. PCT/EP00/08784 on Sep. 7, 2000.

(30) Foreign Application Priority Data

Sep. 7, 1999 (GB) ............................................. 9921146

(51) Int. Cl.
*A61K 39/12* (2006.01)

(52) U.S. Cl. ................................ 424/204.1; 424/278.1; 530/300; 435/6

(58) Field of Classification Search .............. 424/204.1, 424/278.1; 435/345, 6; 530/30

See application file for complete search history.

(56) References Cited

U.S. PATENT DOCUMENTS

| | | | |
|---|---|---|---|
| 5,151,023 | A | 9/1992 | Kuzuhara et al. |
| 5,855,891 | A | 1/1999 | Lowy et al. |
| 6,123,948 | A * | 9/2000 | Whittle et al. ........... 424/204.1 |
| 6,251,678 | B1 * | 6/2001 | Volkin et al. .................. 436/8 |

FOREIGN PATENT DOCUMENTS

| | | | |
|---|---|---|---|
| EP | 689454 B1 | | 9/1994 |
| WO | WO 95/17209 | | 6/1995 |
| WO | WO 96/26277 | * | 8/1996 |
| WO | WO 99/10375 | * | 3/1999 |
| WO | WO 99/45957 | | 9/1999 |
| WO | WO 00/15255 | | 3/2000 |
| WO | WO 00/23105 | | 4/2000 |
| WO | WO/44944 | | 7/2000 |

OTHER PUBLICATIONS

Thompson et al (Biochemical Society Transactions, 1997, 274S).*
Roden et al., "Assessment of the SerologicalRelatedness of Genital Human Papillomaviruses by Hemagglutination Inhibition", Journal of Virology, vol. 70, n0.5, May 1996, pp. 3298–3301.
Wheeler, "Preventive Vaccines for Cervical Cancer", Salud Publica De Mexico, vol. 39, No. 4, Jul. 1997, pp. 283–287.
Schiller et al., "Papillomavirus–Like Particles and HPV Vaccine Development", Seminars in Cancer biology, Saunders Scientific Publications, vol. 7, No. 6, pp. 373–382.
Suzich et al., "Systemtic immunication with papilomavirus L1 protein completely prevents the development of viral mucosal papillomas", Proceedings of the National Academy of Sciences of USA, National Academy of Science, vol. 92, 1995, pp. 11553–11557.
Lowe et al., "Human Papillomavirus Type 11 (HPV–11) Neutralizing Antibodies in the Serum and Genital Mucosal Secretions of African Green Monkeys Immunized with HPV–11 Virus–Like Particles Expressed in Yeast", Journal of Infectious Diseases, vol. 176, No. 5, 1997 pp. 1141–1145.
U.S. Appl. No. 09/807,657, filed Apr. 16, 2001, Garcon.
Breitburd et al., Immunization with Virus–Like Particles from Cottontail Rabbit Papillomavirus (CRPV) Can Protect Against Experimental CRPV Infection, Journal of Virology, vol. 69, (1995), pp. 3959–3963.
Harper et al., Lancet, vol. 364, (2004), pp. 1757–1765.
Kirnbauer et al., Virus–Like Particles of Bovine Papillomavirus Type 4 in Prophylactic and Therapeutic Immunization, Virology, vol. 219, (1996), pp. 37–44.
Kirnbauer et al., Papillomavirus L1 Major Capsid Protein Self–Assembles into Virus–Like Particles that are Highly Immunogenic, PNAS, (1992), vol. 89, pp. 12180–12184.

* cited by examiner

*Primary Examiner*—Ali R. Salimi
(74) *Attorney, Agent, or Firm*—William E. Majarian; Stephen Venetianer; Charles Kinzig

(57) ABSTRACT

Novel combined vaccine compositions are provided, comprising a herpes simplex virus (HSV) antigen and a HPV antigen and optionally in addition one or more of the following: an EBV antigen, a hepatitis A antigen or inactivated attenuated virus, a hepatitis B viral antigen, a VZV antigen, a HCMV antigen, a *Toxoplasma gondii* antigen. The vaccine compositions are formulated with an adjuvant which is a preferential stimulator of TH1 cell response such as 3D-MPL and QS21.

6 Claims, 8 Drawing Sheets

FIGURE 1: Anti-VLP16 response at day 14 post II
Results on individual sera (EU/ml)
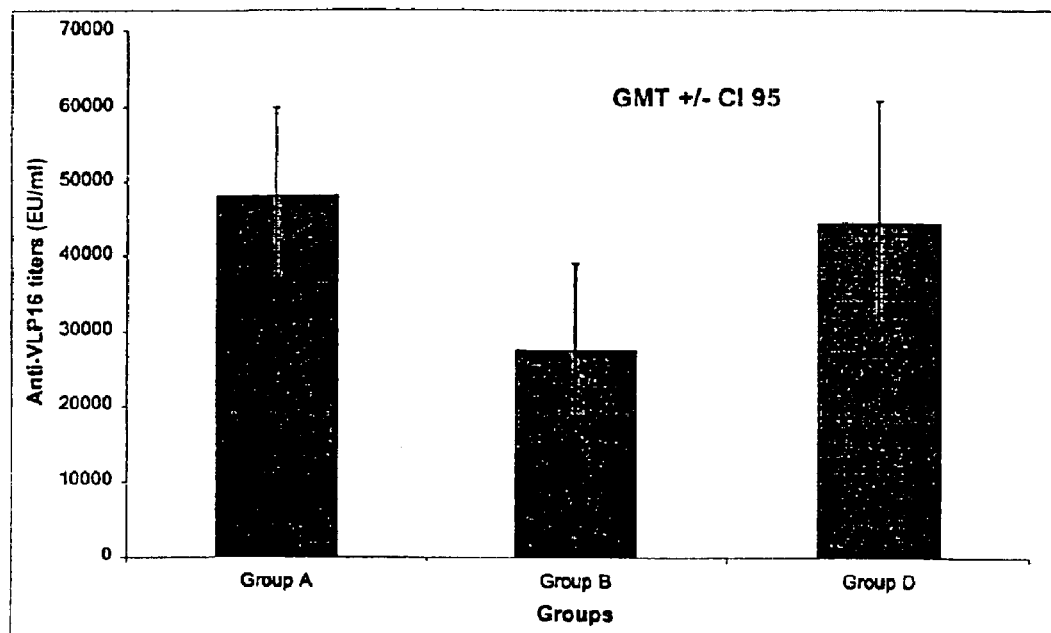

FIGURE 2: Anti-VLP18 response at day 14 post II
Results on individual sera (EU/ml)
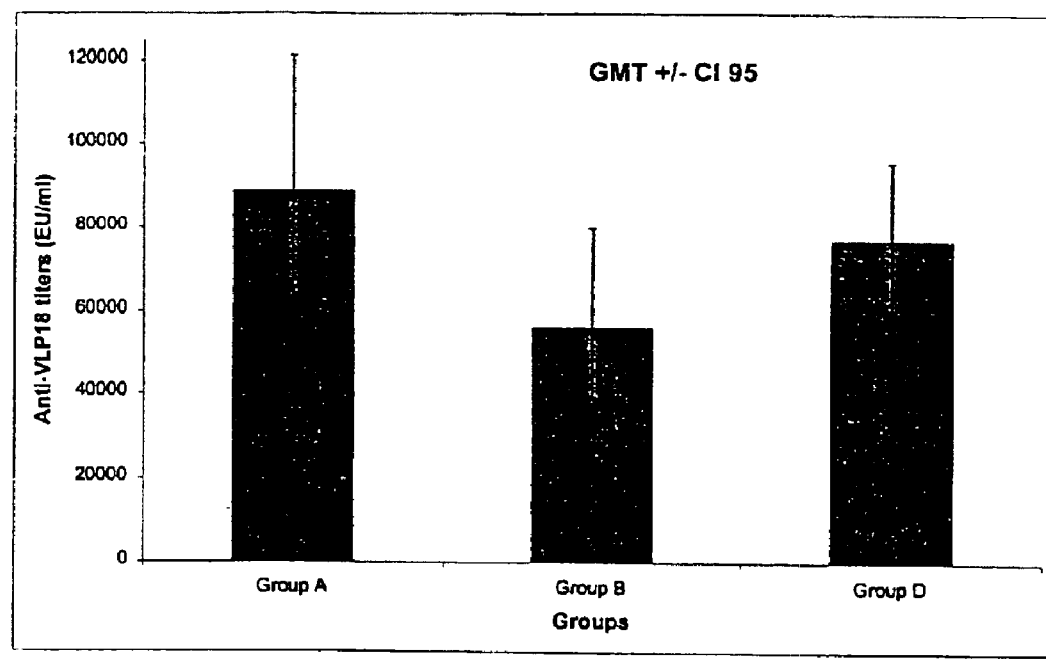

FIGURE 3: Anti-gD response at day 14 post II
Results on individual sera (EU/ml)
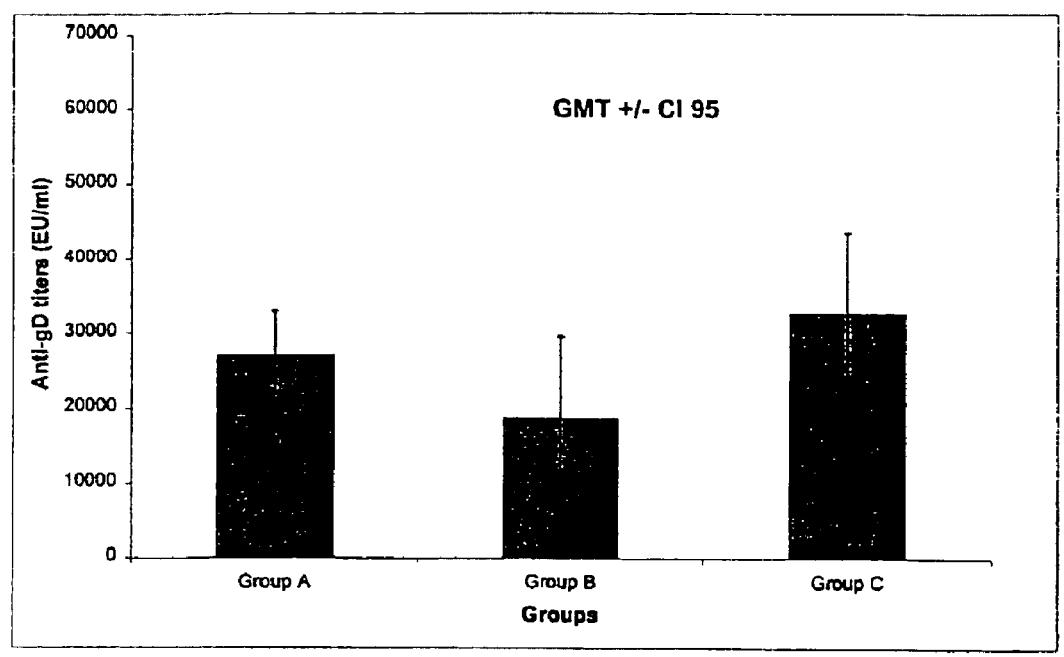

FIGURE 4 : Anti-HBs response at day 14 post II
Results on individual sera (EU/ml)
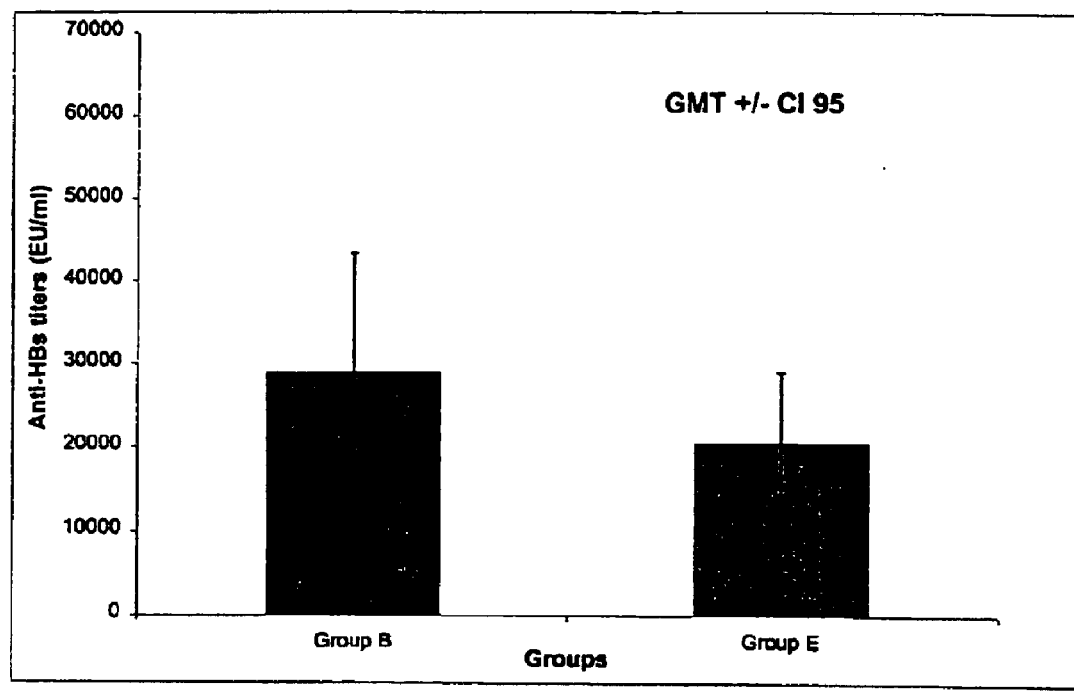

FIGURE 5: CYTOKINE RESULTS - DAY 14 POST II
IFN-g production after in vitro stimulation with VLP16
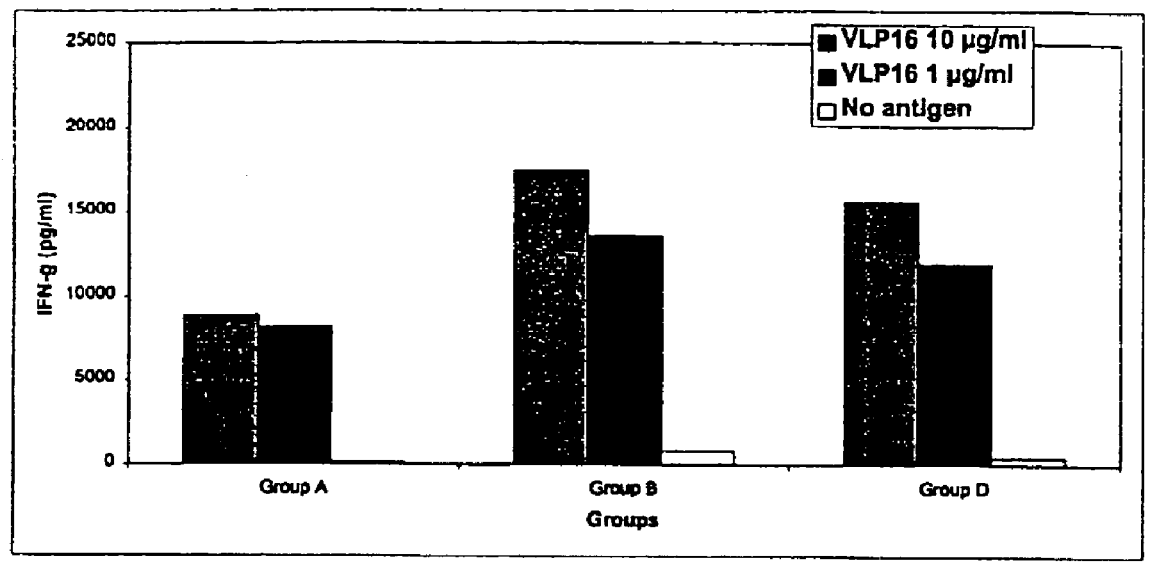
IL-5 production after in vitro stimulation with VLP16
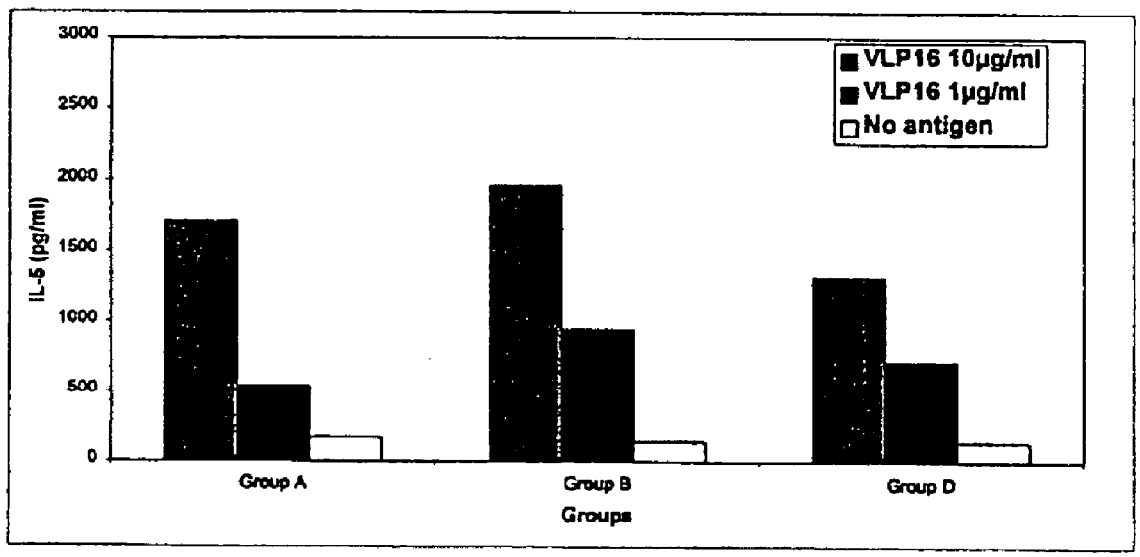

FIGURE 6: CYTOKINE RESULTS DAY 14 POST II
IFN-g production after in vitro stimulation with VLP18
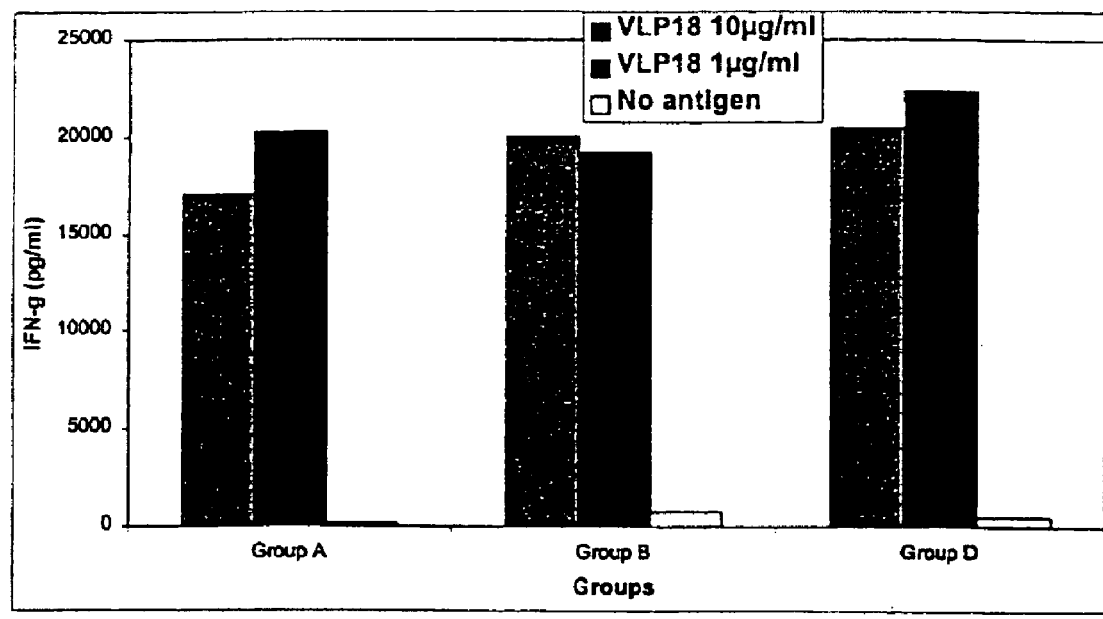
IL-5 production after in vitro stimulation with VLP18
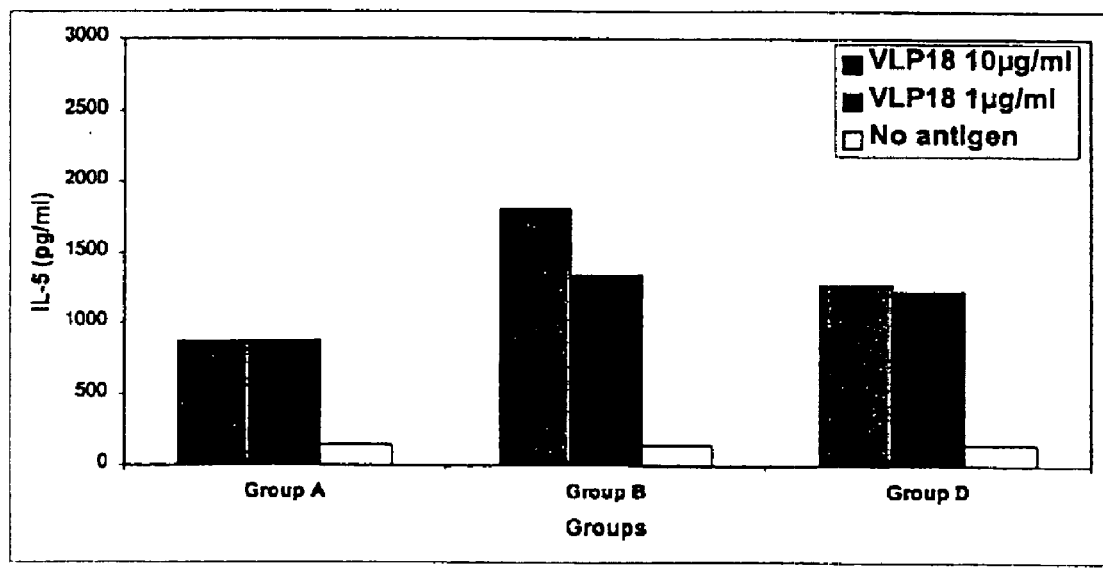

FIGURE 7: CYTOKINE RESULTS - DAY 14 POST II
IFN-g production after in vitro stimulation with gD
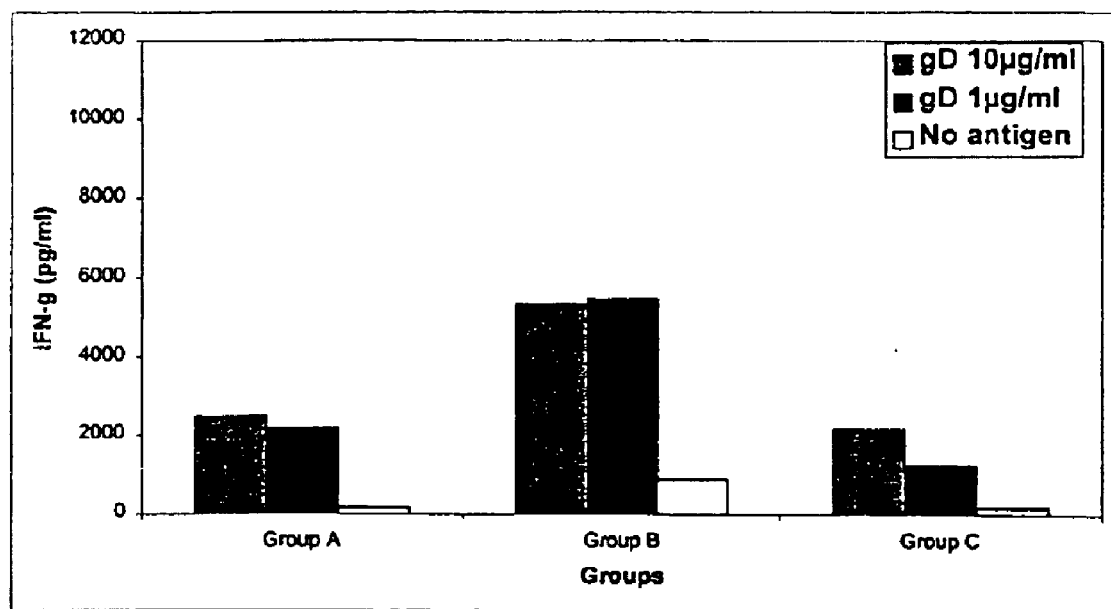
IL-5 production after in vitro stimulation with gD
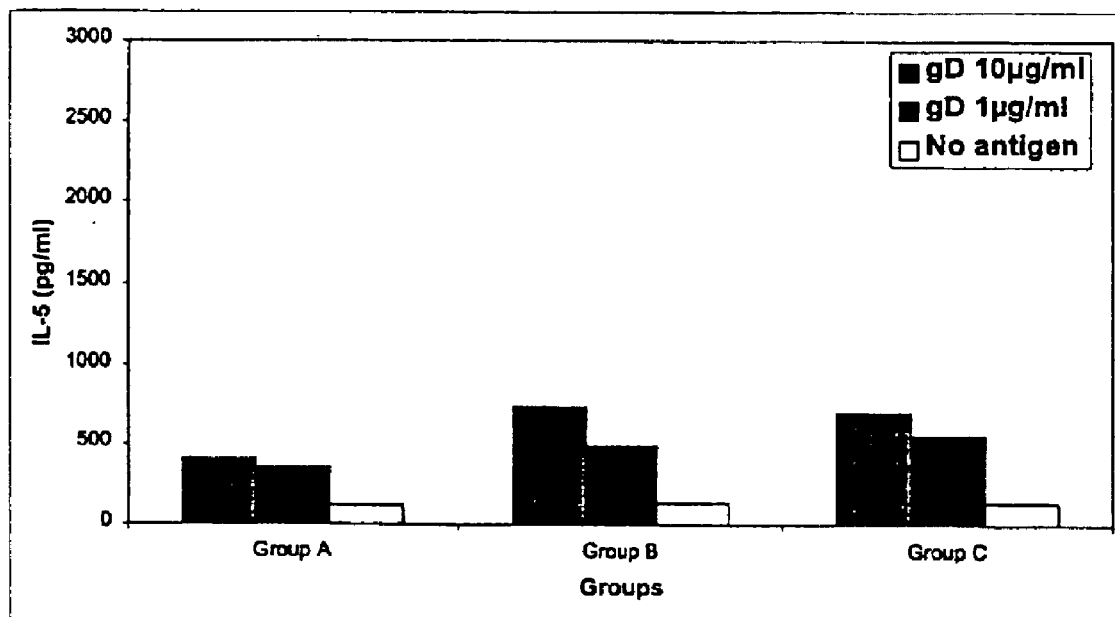

FIGURE 8: CYTOKINE RESULTS - DAY 14 POST II
IFN-g production after in vitro stimulation with HBs
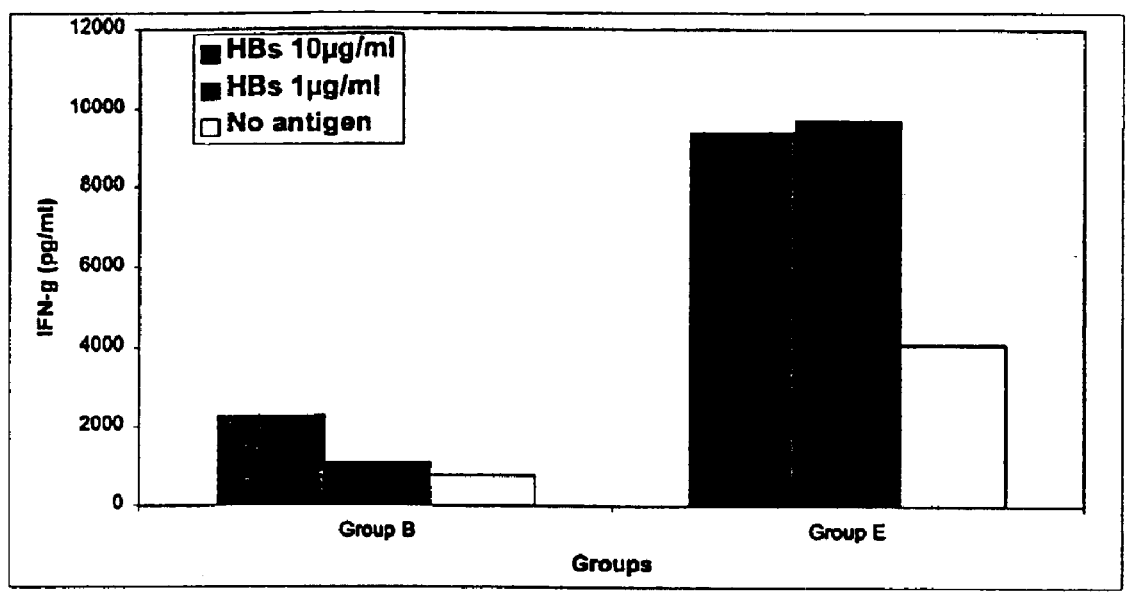
IL-5 production after in vitro stimulation with HBs
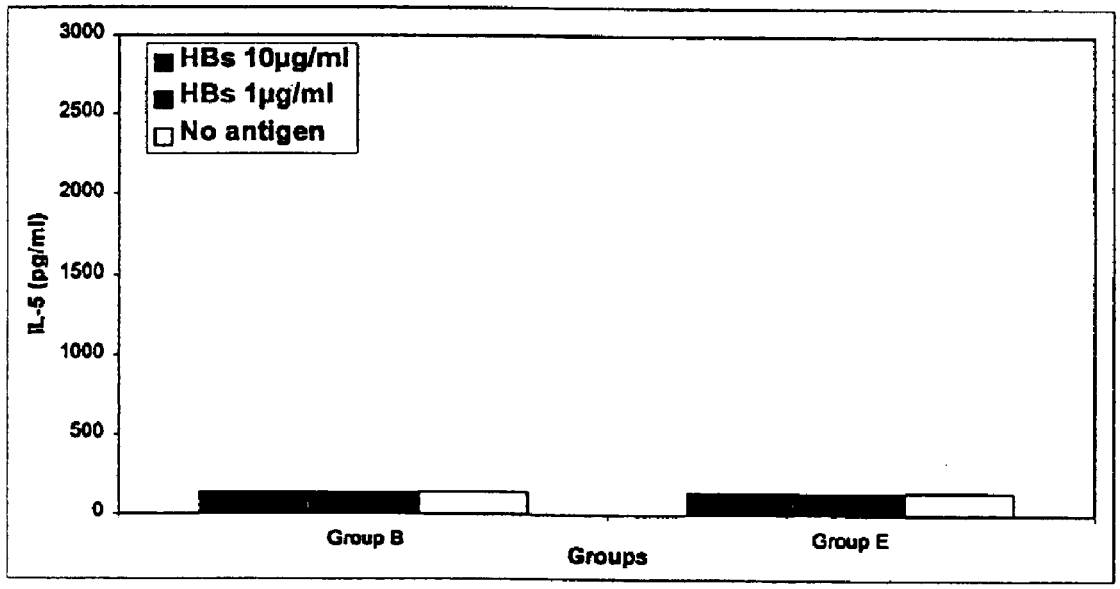

COMBINATION VACCINE FOR ADMINISTRATION TO ADOLESCENTS

This is a divisional of application Ser. No. 10/070,479 filed 26 Jun. 2002 (pending), which is a §371 national stage filing of PCT/EP00/08784 filed Sep. 7, 2000.

This invention relates to novel vaccine formulations, methods for preparing them and their use in therapy. In particular the present invention relates to combination vaccines for administration to adolescents.

Papillomaviruses are small DNA tumour viruses, which are highly species specific. So far, over 70 individual human papillomavirus (HPV) genotypes have been described. HPVs are generally specific either for the skin (e.g. HPV-1 and -2) or mucosal surfaces (e.g. HPV-6 and -11) and usually cause benign tumours (warts) that persist for several months or years. Such benign tumours may be distressing for the individuals concerned but tend not to be life threatening, with a few exceptions.

Some HPVs are also associated with cancers. The strongest positive association between an HPV and human cancer is that which exists between HPV-16 and HPV-18 and cervical carcinoma. Cervical cancer is the most common malignancy in developing countries, with about 500,000 new cases occurring in the world each year. It is now technically feasible to actively combat primary HPV-16 infections, and even established HPV-16-containing cancers, using vaccines. For a review on the prospects for prophylactic and therapeutic vaccination against HPV-16 see Cason J., Clin. Immunother. 1994; 1(4) 293–306 and Hagenesee M. E., Infections in Medicine 1997 14(7) 555–556,559–564.

Other HPVs of particular interest are serotypes 31,33 and 45.

Today, the different types of HPVs have been isolated and characterised with the help of cloning systems in bacteria and more recently by PCR amplification. The molecular organisation of the HPV genomes has been defined on a comparative basis with that of the well-characterised bovine papillomavirus type 1 (BPV1).

Although minor variations do occur, all HPVs genomes described have at least seven early genes, E1 to E7 and two late genes L1 and L2. In addition, an upstream regulatory region harbors the regulatory sequences which appear to control most transcriptional events of the HPV genome.

E1 and E2 genes are involved in viral replication and transcriptional control, respectively and tend to be disrupted by viral integration. E6 and E7, and recent evidence implicate also E5 are involved in viral transformation.

In the HPVs involved in cervical carcinoma such as HPV 16 and 18, the oncogenic process starts after integration of viral DNA. The integration results in the inactivation of genes coding for the capsid proteins L1 and L2 and in installing continuous over expression of the two early proteins E6 and E7 that will lead to gradual loss of the normal cellular differentiation and the development of the carcinoma.

Carcinoma of the cervix is common in women and develops through a pre-cancerous intermediate stage to the invasive carcinoma which frequently leads to death. The intermediate stages of the disease is known as cervical intraepithelial neoplasia and is graded I to III in terms of increasing severity.

Clinically, HPV infection of the female anogenital tract manifests as cervical flat condylomas, the hallmark of which is the koilocytosis affecting predominantly the superficial and intermediate cells of the cervical squamous epithelium. Koilocytes which are the consequence of a cytopathic effect of the virus, appear as multinucleated cells with a perinuclear clear halo. The epithelium is thickened with abnormal keratinisation responsible for the warty appearance of the lesion.

Such flat condylomas when positive for the HPV 16 or 18 serotypes, are high-risk factors for the evolution toward cervical intraepithelial neoplasia (CIN) and carcinoma in situ (CIS) which are themselves regarded as precursor lesions of invasive cervix carcinoma.

WO 96/19496 discloses variants of human papilloma virus E6 and E7 proteins, particularly fusion proteins of E6/E7 with a deletion in both the E6 and E7 proteins. These deletion fusion proteins are said to be immunogenic.

HPV L1 based vaccines are disclosed in WO94/00152, WO94/20137, WO93/02184 and WO94/05792. Such a vaccine can comprise the L1 antigen as a monomer, a capsomer or a virus like particle. Such particles may additionally comprise L2 proteins. L2 based vaccines are described for example in WO93/00436. Other HPV vaccines are based on the Early proteins, such as E7 or fusion proteins such as L2-E7.

HSV-2 is the primary etiological agent of herpes genitalis. HSV-2 and HSV-1 (the causative agent of herpes labialis) are characterised by their ability to induce both acute diseases and to establish a latent infection, primarily in neuronal ganglia cells.

Genital herpes is estimated to occur in about 5 million people in the U.S.A. alone with 500,000 clinical cases recorded every year (primary and recurrent infection). Primary infection typically occurs after puberty and is characterised by the localised appearance of painful skin lesions, which persist for a period of between 2 to 3 weeks. Within the following six months after primary infection 50% of patients will experience a recurrence of the disease. About 25% of patients may experience between 10–15 recurrent episodes of the disease each year. In immunocompromised patients the incidence of high frequency recurrence is statistically higher than in the normal patient population.

Both HSV-1 and HSV-2 virus have a number of glycoprotein components located on the surface of the virus. These are known as gB, gC, gD and gE etc.

There is a need for effective combination vaccines to prevent diseases to which adolescents are particularly prone.

The present invention provides a vaccine composition comprising:
(a) a herpes simplex virus (HSV) antigen; and
(b) a human papillomavirus (HPV) antigen
in combination with an adjuvant which is a preferential stimulator of TH1 cell response.

The vaccine composition of the invention is of great benefit for administration to adolescents who may be particularly at risk of HSV, and/or HPV infection.

Optionally the vaccine composition of the invention additionally comprises one or more of a number of other antigens as described below.

It has been found that the vaccine compositions according to the invention surprisingly show no interference, that is to say that the immune response to each antigen in the composition of the invention is essentially the same as that which is obtained by each antigen given individually in conjunction with an adjuvant which is a preferential stimulator of TH1 cell response.

Vaccines for the prophylaxis of hepatitis B infections, comprising one or more hepatitis B antigens, are well known. For example the vaccine Engerix-B (Trade Mark) from SmithKline Beecham Biologicals is used to prevent Hepatitis B. This vaccine comprises hepatitis B surface antigen (specifically the 226 amino acid S-antigen described in Harford et. al. in Postgraduate Medical Journal, 1987, 63 (Suppl. 2), p65–70) and is formulated using aluminium hydroxide as adjuvant.

The vaccine Havrix (Trade Mark), also from SmithKline Beecham Biologicals is an example of a vaccine that can be used to prevent hepatitis A infections. It is formulated with aluminium hydroxide as adjuvant. This vaccine comprises an attenuated strain of the HM-175 Hepatitis A virus inactivated with formol (formaldehyde); see Andre et. al. (Prog. med. Virol., vol. 37, p1–24).

As used herein, the term hepatitis A viral (HAV) antigen is used to refer to either a protein derived from hepatitis A virus or an attenuated strain of HAV, optionally inactivated, e.g. with formaldehyde. If the HAV antigen is a protein derived from hepatitis A virus it may optionally be a recombinant protein.

The vaccine Twinrix (Trade Mark) is a combination of a recombinant hepatitis B anitgen with the aforementioned inactivated attenuated hepatitis A virus. The vaccine may be used to protect against hepatitis A and hepatitis B simultaneously.

European patent 0 339 667 (Chemo Sero) describes the general concept of combining a hepatitis A antigen and a hepatitis B antigen to make a combination vaccine. In that specification it is stated that the adjuvant which is used is not critical: it must only be capable of enhancing the immune activity to a desired extent and not cause any side-effects. It is stated that aluminium gel may be used, in particular aluminium hydroxide gel and aluminium phosphate gel.

The vaccine composition according to the invention may comprises, in addition the HPV and HSV antigens, an HAV antigen or a HBV antigen or more preferably a combination of both an HAV and an HBV antigen Such a vaccine is of great benefit for administration to adolescents who may be particularly at risk of HSV, and/or HPV infection, and/or HAV infection, and/or HBV infection.

An immune response may be broadly divided into two extreme catagories, being a humoral or cell mediated immune response (traditionally characterised by antibody and cellular effector mechanisms of protection respectively). These categories of response have been termed TH1-type responses (cell-mediated response), and TH2-type immune responses (humoral response).

Extreme TH1-type immune responses may be characterised by the generation of antigen specific, haplotype restricted cytotoxic T lymphocytes, and natural killer cell responses. In mice TH1-type responses are often characterised by the generation of antibodies of the IgG2a subtype, whilst in the human these correspond to IgG1 type antibodies. TH2-type immune responses are characterised by the generation of a range of immunoglobulin isotypes including in mice IgG1.

It can be considered that the driving force behind the development of these two types of immune responses are cytokines. High levels of TH1-type cytokines tend to favour the induction of cell mediated immune responses to the given antigen, whilst high levels of TH2-type cytokines tend to favour the induction of humoral immune responses to the antigen.

The distinction of TH1 and TH2-type immune responses is not absolute. In reality an individual will support an immune response which is described as being predominantly TH1 or predominantly TH2. However, it is often convenient to consider the families of cytokines in terms of that described in murine CD4 +ve T cell clones by Mosmann and Coffman (Mosmann, T. R. and Coffman, R. L. (1989) *TH1 and TH2 cells: different patterns of lymphokine secretion lead to different functional properties. Annual Review of Immunology*, 7, p145–173). Traditionally, TH1-type responses are associated with the production of the INF-γ cytokines by T-lymphocytes. Other cytokines often directly associated with the induction of TH1-type immune responses are not produced by T-cells, such as IL-12. In contrast, TH2-type responses are associated with the secretion of IL-4, IL-5, IL-6, IL-10 and tumour necrosis factor-β(TNF-β).

It is known that certain vaccine adjuvants are particularly suited to the stimulation of either TH1 or TH2-type cytokine responses. Traditionally the best indicators of the TH1:TH2 balance of the immune response after a vaccination or infection includes direct measurement of the production of TH1 or TH2 cytokines by T lymphocytes in vitro after restimulation with antigen, and/or (at least in mice) the measurement of the IgG1:IgG2a ratio of antigen specific antibody responses.

Thus, a TH1-type adjuvant is one which stimulates isolated T-cell populations to produce high levels of TH1-type cytokines when re-stimulated with antigen in vitro, and induces antigen specific immunoglobulin responses associated with TH1-type isotype.

Adjuvants which are capable of preferential stimulation of the TH1 cell response are described in International Patent Application No. WO 94/00153 and WO 95/17209.

3 De-O-acylated monophosphoryl lipid A (3D-MPL) is one such adjuvant. This is known from GB 2220211 (Ribi). Chemically it is a mixture of 3 De-O-acylated monophosphoryl lipid A with 4, 5 or 6 acylated chains and is manufactured by Ribi Immunochem, Montana. A preferred form of 3 De-O-acylated monophosphoryl lipid A is disclosed in European Patent 0 689 454 B1 (SmithKline Beecham Biologicals SA).

Preferably, the particles of 3D-MPL are small enough to be sterile filtered through a 0.22 micron membrane (as described in European Patent number 0 689 454). 3D-MPL will be present in the range of 10 μg–100 μg preferably 25–50 μg per dose wherein the antigen will typically be present in a range 2–50 μg per dose.

Another preferred adjuvant comprises QS21, an Hplc purified non-toxic fraction derived from the bark of Quillaja Saponaria Molina. Optionally this may be admixed with 3 De-O-acylated monophosphoryl lipid A (3D-MPL), optionally together with an carrier.

The method of production of QS21 is disclosed in U.S. Pat. No. 5,057,540.

Non-reactogenic adjuvant formulations containing QS21 have been described previously (WO 96/33739). Such formulations comprising QS21 and cholesterol have been shown to be successful TH1 stimulating adjuvants when formulated together with an antigen. Thus vaccine compositions which form part of the present invention may include a combination of QS21 and cholesterol.

Further adjuvants which are preferential stimulators of TH1 cell response include immunomodulatory oligonucleotides, for example unmethylated CpG sequences as disclosed in WO 96/02555.

Combinations of different TH1 stimulating adjuvants, such as those mentioned hereinabove, are also contemplated as providing an adjuvant which is a preferential stimulator of TH1 cell response. For example, QS21 can be formulated together with 3D-MPL. The ratio of QS21:3D-MPL will typically be in the order of 1:10 to 10:1; preferably 1:5 to 5:1 and often substantially 1:1. The preferred range for optimal synergy is 2.5:1 to 1:13D-MPL: QS21.

Preferably a carrier is also present in the vaccine composition according to the invention. The carrier may be an oil in water emulsion, or an aluminium salt, such as aluminium phosphate or aluminium hydroxide.

A preferred oil-in-water emulsion comprises a metabolisible oil, such as squalene, alpha tocopherol and Tween 80. Additionally the oil in water emulsion may contain span 85 and/or lecithin and/or tricaprylin.

In a particularly preferred aspect the antigens in the vaccine composition according to the invention are combined with 3D-MPL and alum.

Typically for human administration QS21 and 3D-MPL will be present in a vaccine in the range of 1 μg–200 μg, such as 10–100 μg, preferably 10 μg–50 μg per dose. Typically the oil in water will comprise from 2 to 10% squalene, from 2 to 10% alpha tocopherol and from 0.3 to 3% tween 80. Preferably the ratio of squalene: alpha tocopherol is equal to or less than 1 as this provides a more stable emulsion. Span 85 may also be present at a level of 1%. In some cases it may be advantageous that the vaccines of the present invention will further contain a stabiliser.

Non-toxic oil in water emulsions preferably contain a non-toxic oil, e.g. squalane or squalene, an emulsifier, e.g. Tween 80, in an aqueous carrier. The aqueous carrier may be, for example, phosphate buffered saline.

A particularly potent adjuvant formulation involving QS21, 3D-MPL and tocopherol in an oil in water emulsion is described in WO 95/17210.

The HPV antigen in the composition of the invention is preferably derived from HPV 16 and/or 18, or from HPV 6 and/or 11, or HPV 31, 33 or 45.

In one preferred embodiment the HPV antigen in the vaccine composition according to the invention comprises the major capsid protein L1 of HPV and optionally the L2 protein, particularly from HPV 16 and/or HPV 18. In this embodiment, the preferred form of the L1 protein is a truncated L1 protein. Preferably the L1, optionally in a L1-L2 fusion, is in the form of a virus-like particle (VLP). The L1 protein may be fused to another HPV protein, in particular E7 to form an L1-E7 fusion. Chimeric VLPs comprising L1-E or L1-L2-E are particularly preferred.

In another preferred embodiment, the HPV antigen in the composition of the invention is derived from an E6 or E7 protein, in particular E6 or E7 linked to an immunological fusion partner having T cell epitopes.

In a preferred form of this embodiment of the invention, the immunological fusion partner is derived from protein D of *Heamophilus influenza* B. Preferably the protein D derivative comprises approximately the first ⅓ of the protein, in particular approximately the first N-terminal 100–110 amino acids.

Preferred fusion proteins in this embodiment of the invention comprise Protein D-E6 from HPV 16, Protein D-E7 from HPV 16 Protein D-E7 from HPV 18 and Protein D-E6 from HPV 18. The protein D part preferably comprises the first ⅓ of protein D.

In still another embodiment of the invention, the HPV antigen is in the form of an L2-E7 fusion, particularly from HPV 6 and/or HPV 11.

The proteins of the present invention preferably are expressed in *E. coli*. In a preferred embodiment the proteins are expressed with a Histidine tail comprising between 5 to 9 and preferably six Histidine residues. These are advantageous in aiding purification. The description of the manufacture of such proteins is fully described in co-pending UK patent application number GB 9717953.5.

The HPV antigen in the vaccine composition may be adsorbed onto $Al(OH)_3$.

The HSV antigen in the composition of the invention is preferably derived from HSV-2, typically glycoprotein D. Glycoprotein D is located on the viral membrane, and is also found in the cytoplasm of infected cells (Eisenberg R. J. et al; J of Virol 1980, 35, 428–435). It comprises 393 amino acids including a signal peptide and has a molecular weight of approximately 60 kD. Of all the HSV envelope glycoproteins this is probably the best characterised (Cohen et al; J. of Virology, 60, 157–166). In vivo it is known to play a central role in viral attachment to cell membranes. Moreover, glycoprotein D has been shown to be able to elicit neutralising antibodies in vivo (Eing et al J. Med. Virology 127: 59–65). However, latent HSV-2 virus can still be reactivated and induce recurrence of the disease despite the presence of high neutralising antibodies titre in the patients sera.

In a preferred embodiment of the invention the HSV antigen is a truncated HSV-2 glycoprotein D of 308 amino acids which comprises amino acids 1 through 306 naturally occurring glycoprotein with the addition Asparagine and Glutamine at the C terminal end of the truncated protein devoid of its membrane anchor region. This form of the protein includes the signal peptide which is cleaved to yield a mature 283 amino acid protein. The production of such a protein in Chinese Hamster ovary cells has been described in Genentech's European patent EP-B-139 417.

The recombinant mature HSV-2 glycoprotein D truncate is preferably used in the vaccine formulations of the present invention and is designated rgD2t.

A combination of this HSV-2 antigen in combination with the adjuvant 3D-MPL has been described in WO 92/16231

When a hepatitis B viral (HBV) antigen is included in the composition of the invention this is typically hepatitis B surface antigen.

The preparation of Hepatitis B surface antigen (HBsAg) is well documented. See for example, Harford et.al. in Develop. Biol. Standard 54, page 125 (1983), Gregg et.al. in Biotechnology, 5, page 479 (1987), EP-A-0 226 846, EP-A-0 299 108 and references therein.

As used herein the expression 'Hepatitis B surface antigen', abbreviated herein to 'HBsAg' or 'HBS' includes any HBsAg antigen or fragment thereof displaying the antigenicity of HBV surface antigen. It will be understood that in addition to the 226 amino acid sequence of the HBsAg S antigen (see Tiollais et. al. Nature, 317, 489 (1985) and references therein) HBsAg as herein described may, if desired, contain all or part of a pre-S sequence as described in the above references and in EP-A-0 278 940. HBsAg as herein described can also refer to variants, for example the 'escape mutant' described in WO 91/14703. In a further aspect the HBsAg may comprise a protein described as L* in European Patent Application Number 0 414 374, that is to say a protein, the amino acid sequence of which consists of parts of the amino acid sequence of the hepatitis B virus large (L) protein (ad or ay subtype), characterised in that the amino acid sequence of the protein consists of either:
  (a) residues 12–52, followed by residues 133–145, followed by residues 175–400 of the said L protein; or
  (b) residue 12, followed by residues 14–52, followed by residues 133–145, followed by residues 175–400 of the said L protein.

HBsAg may also refer to polypeptides described in EP 0 198 474 or EP 0 304 578.

Normally the HBsAg will be in particle form. It may comprise S protein alone or may be as composite particles, for example (L*,S) wherein L* is as defined above and S denotes the S-protein of hepatitis B surface antigen.

The HBsAg may be adsorbed on aluminium phosphate as described in WO93/24148.

Preferably an hepatitis B (HBV) antigen used in the formulation of the invention is HBsAg S-antigen as used in the commercial product Engerix-B (Trade Mark; SmithKline Beecham Biologicals).

A vaccine comprising hepatitis B surface antigen in conjunction with 3D-MPL was described in European Patent Application 0 633 784.

Examples of antigens from additional pathogens which may be included in the compositions according to the invention are now described.

Epstein Barr Virus (EBV), a member of the herpesvirus group, causes infectious mononucleosis as a primary disease in humans. Predominantly it affects children or young adults. More than 90% of the average adult population is infected by EBV that persists for lifetime in peripheral B-lymphocytes. The virus is lifelong produced in the parotid gland and spread primarily by exchange of saliva from individuals who shed the virus. Children infected with EBV are largely asymptomatic or have very mild symptoms, while adolescents and adults who become infected develop typical infectious mononucleosis, characterised by fever, pharyngitis, and adenopathy. People who have been infected maintain anti-EBV antibodies for the remainder of their lives, and are thus immune to further infection.

In addition to its infectious qualities, EBV has been shown to transform lymphocytes into rapidly dividing cells and has therefore been implicated in several different lymphomas, including African Burkitt's lymphoma (BL). EBV may also be involved in causing nasopharyngeal carcinoma (NPC). Worldwide it is estimated that 80,000 cases of nasopharyngeal carcinoma occur and it is more prevalent in ethnic Chinese populations. Infectious mononucleosis is a consequence of primary infection by EBV. It is not a life-threatening disease if additional risk factors are absent.

Four proteins of the EBV viral envelope constituting the so-called membrane antigen complex have been described. They are usually referred to as gp 220/350 or gp 250/350 or simply as gp 250 or 350 (see EP-A-151079). There is convincing evidence that gp 350 and gp 250 induce the production of neutralising antibodies and that antibodies against gp 350 and gp 250 have neutralising capacity. These proteins are thus candidates for a possible EBV vaccine. For further information about the application of gp 250/350 for prophylaxis and treatment of EBV-related diseases see EP 0 173 254.

The major EBV surface glycoprotein gp350/220 infects human target cells through interaction with the cellular membrane protein, CD21. Gp350/220 is the primary target for EBV-neutralising antibodies in humans and some forms of gp350/220 have been shown to protect against EBV-related disease. Preferably a vaccine composition according to the invention comprises gp 350 of EBV although other protective antigens may be used.

In a preferred aspect the vaccine composition of the invention additionally comprises a Varicella Zoster viral antigen (VZV antigen). Suitable antigens of VZV for inclusion in the vaccine formulation include gpI-V described by Longnecker et al., Proc Natl Acad Sci USA 84, 4303–4307 (1987).

In a preferred embodiment gpI (see Ellis et al., U.S. Pat. No. 4,769,239) is used. See also European Patent No. 0 405 867 B1.

In another preferred aspect the vaccine composition of the invention additionally comprises a human cytomegalovirus (HCMV) antigen. HCMV is a human DNA virus belonging to the family of herpes viruses. HCMV is endemic in most parts of the world. Among two populations, HCMV is responsible for serious medical conditions. HCMV is a major cause of congenital defects in new borns. The second population at risk are immunocompromised patients such as those suffering from HIV infection and those patients undergoing transplantations. The clinical disease causes a variety of symptoms including fever, hepatitis, pneumonitis and infectious mononucleosis. A preferred antigen for use in a vaccine against HCMV is gB685** as described in WO 95/31555. Immunogens for use in HCMV vaccines are also provided by pp65, an HCMV Matrix Protein as described in WO 94/00150 (City of Hope).

In one preferred aspect the vaccine composition of the invention additionally comprises both a VZV and an HCMV antigen, in particular those antigens described above.

In another preferred aspect the vaccine composition of the invention additionally comprises a *Toxoplasma gondii* antigen. *Toxoplasma gondii* is an obligate intracellular protozoan parasite responsible for toxoplasmosis in warm-blooded animals, including man. Although it is generally clinically asymptomatic in healthy individuals, toxoplasmosis may cause severe complications in pregnant women and immunocompromised patients. A preferred antigen for use in a vaccine against *Toxoplasma gondii* is SAG1 (also known as P30) as described in WO96/02654 or Tg34 as described in WO92/11366.

In one preferred aspect the vaccine composition of the invention additionally comprises either a VZV antigen or an HCMV antigen combined with a *Toxoplasma gondii* antigen, in particular those antigens described above.

In a preferred aspect the vaccine composition of the invention is a multivalent vaccine, for example a tetra- or pentavalent vaccine.

The formulations of the present invention are very effective in inducing protective immunity, even with very low doses of antigen (e.g. as low as 5 µg rgD2t).

They provide excellent protection against primary infection and stimulate, advantageously both specific humoral (neutralising antibodies) and also effector cell mediated (DTH) immune responses.

The present invention in a further aspect provides a vaccine formulation as herein described for use in medical therapy, particularly for use in the treatment or prophylaxis of human papillomavirus infections and herpes simplex virus infections.

The vaccine of the present invention will contain an immunoprotective quantity of the antigens and may be prepared by conventional techniques.

Vaccine preparation is generally described in Pharmaceutical Biotechnology, Vol.61 Vaccine Design—the subunit and adjuvant approach, edited by Powell and Newman, Plenurn Press, 1995. New Trends and Developments in Vaccines, edited by Voller et al., University Park Press, Baltimore, Maryland, U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372, 945 and by Armor et al., U.S. Pat. No. 4,474,757.

The amount of protein in each vaccine dose is selected as an amount which induces an immunoprotective response without significant, adverse side effects in typical vaccinees. Such amount will vary depending upon which specific immunogen is employed. Generally, it is expected that each dose will comprise 1–1000 μg of protein, preferably 2–100 μg, most preferably 4–40 μg. An optimal amount for a particular vaccine can be ascertained by standard studies involving observation of antibody titres and other responses in subjects. Following an initial vaccination, subjects may receive a boost in about 4 weeks.

In addition to vaccination of persons susceptible to HPV or HSV infections, the pharmaceutical compositions of the present invention may be used to treat, immunotherapeutically, patients suffering from the said viral infections.

In a further aspect of the present invention there is provided a method of manufacture as herein described, wherein the method comprises mixing a human papilloma virus antigen and a herpes simplex virus antigen with a TH-1 inducing adjuvant, for example 3D-MPL and, preferably, a carrier, for example alum.

If desired, other antigens may be added, in any convenient order, to provide multivalent vaccine compositions as described herein.

The following example illustrates but does not limit the invention.

EXAMPLE 1

Comparative Immunogenicity of HPV Ags/HBs/gD in Monovalent or Combination Vaccines Formulated with AS04.

Introduction

An immunogenicity study was performed in Balb/C mice using four different antigens:

1. HPV16 L1 Virus Like Particle (VLP-16)
2. HPV18 L1 Virus Like Particle (VLP-18)
3. gD antigen of HSV-2
4. HBsAg formulated with Alum/3D-MPL (AS04) using pre adsorbed monobulks of antigen or 3D-MPL on Al(OH)$_3$ or AlPO$_4$.

3D-MPL/Al(OH)$_3$ formulations are referred to AS04D whereas 3D-MPL/AlPO$_4$ based formulations are referred to AS04C.

The following vaccines were assessed:

1. VLP16+VLP18 AS04D;
2. gD AS04D;
3. HBs AS04C.

and the potential to combine these vaccines was evaluated.

The aim of this experiment was to compare the immunogenicity of two different AS04 combinations made of either:

1. VLP16+VLP18 and gD.
2. VLP16+VLP18and gD and HBs Ag.

The experimental protocol is fully described in the Material and Methods section.

In summary, groups of 10 mice were immunised intramuscularly twice at 3 week intervals with various Ag based formulations. Antibody response to VLPs, gD and HBs Ag and the isotypic profile induced by vaccination were monitored by ELISA at day 14 post II. At the same timepoint, the cytokine production (IFNγ/IL5) was analysed after in vitro restimulation of splenic cells with either VLPs, gD or HBs antigens.

Materials and Methods

Formulation

Formulation Compositions

VLP16, VLP18, gD and HBs formulated with 3D-MPL on Aluminium salt.

Components Used

| Component | Concentration | Buffer |
|---|---|---|
| HPV 16 VLP | 560 μg/ml | Tris 20 mM/NaCl 500 mM |
| HPV 18 VLP | 550 μg/ml | NaCl 500 mM/NaPO4 20 mM |
| AL(OH)3 | 10380 μg/ml | H2O |
| HBs | 1219 μg/ml | PO4 10 mM/NaCl 150 mM |
| gD | 443 μg/ml | PBS pH 7.4 |
| 3D-MPL | 1170 μg/ml | Water For Injection |
| AlPO4 | 5 mg/ml | NaCl 150 mM |

Adsorption a) VLP Adsorption

VLP 16 and VLP 18 purified bulk are added to Al(OH)$_3$ to obtain a ratio of 2 μg VLP/10 μg Al(OH)3. The mixture is stored between 2–8° C. until final formulation.

b) gD Adsorption

2 μg gD are mixed with 10 μg Al(OH)$_3$. The mixture is stored between 2–8° C. until final formulation.

c) HBs Adsorption

2 μg Hbs are mixed with 10 μg AlPO$_4$. The mixture is stored between 2–8° C. until final formulation.

d) 3D-MPL Adsorption

5 μg 3D-MPL are mixed with 10 μg Al(OH)$_3$. The mixture is stored between 2–8° C. until final formulation.

5 μg 3D-MPL are mixed with 10 μg AlPO$_4$. The mixture is stored between 2–8° C. until final formulation.

Formulation

H$_2$O and NaCl are mixed (10× concentrated) and after 10 minutes of agitation at room temperature, the differents components are added: adsorbed antigen, 3D-MPL adsorbed and Al(OH)$_3$ (See table below). They are shaken at room temperature for 10 minutes and stored at 4° C. until injection.

| Group | Antigen(s) Type | μg | Immunostimulants Type | μg | Vehicle Type | μg |
|---|---|---|---|---|---|---|
| A | gD | 2 | | | Al(OH)3 | 10 |
| | VLP16 | 2 | | | Al(OH)3 | 10 |
| | VLP18 | 2 | | | Al(OH)3 | 10 |
| | | | 3D-MPL | 5 | Al(OH)3 | 10 |
| | | | | | Al(OH)3 | 10 |
| B | gD | 2 | | | Al(OH)3 | 10 |
| | VLP16 | 2 | | | Al(OH)3 | 10 |
| | VLP18 | 2 | | | Al(OH)3 | 10 |
| | HBs | 2 | | | AlPO4 | 10 |
| | | | 3D-MPL | 5 | Al(OH)3 | 10 |
| C | gD | 2 | | | Al(OH)3 | 10 |
| | | | 3D-MPL | 5 | Al(OH)3 | 10 |
| | | | | | Al(OH)3 | 30 |
| D | VLP16 | 2 | | | Al(OH)3 | 10 |
| | VLP18 | 2 | | | Al(OH)3 | 10 |
| | | | 3D-MPL | 5 | Al(OH)3 | 10 |
| | | | | | Al(OH)3 | 20 |
| E | HBs | 2 | | | AlPO4 | 10 |
| | | | 3D-MPL | 5 | Al(OH)3 | 10 |
| | | | | | Al(OH)3 | 30 |

Mice Serology

Anti-VLP-16 and Anti-VLP-18 Serology

The quantitation of anti-VLP16 and anti-VLP18 antibodies was performed by ELISA using VLP16 503/1 (20/12/99) and VLP18 504/2 (25/10/99F) as coating antigens. The antigen and antibody solutions were used at 50 μl per well. The antigen was diluted at a final concentration of 0.5 μg/ml in PBS and was adsorbed overnight at 4° C. to the wells of 96 wells microtiter plates (Maxisorb Immuno-plate, Nunc, Denmark). The plates were then incubated for 1 hr at 37° C. with PBS containing 1% bovine serum albumin. Two-fold dilutions of sera (starting at 1/400dilution) in the saturation buffer were added to the VLP-coated plates and incubated for 1 hr 30 min at 37° C. The plates were washed four times with PBS 0.1% Tween 20 and biotin-conjugated anti-mouse Ig (Amersham, UK) diluted 1/1500 in saturation buffer were added to each well and incubated for 1 hr 30 min at 37° C. After a washing step, streptavidin-biotinylated peroxydase complex (Amersham, UK) diluted 1/1000 in saturation buffer was added for an additional 30 min at 37° C. Plates were washed as above and incubated for 20 min with a solution of o-phenylenediamine (Sigma) 0.04% $H_2O_2$ 0.03% in 0.1% tween 20 0.05M citrate buffer pH4.5. The reaction was stopped with $H_2SO_4$ 2N and read at 490/630 nm. ELISA titers were calculated from a reference by SoftmaxPro (using a four parameters equation) and expressed in EU/ml.

Anti-gD Response

Quantitation of anti-gD antibody was performed by ELISA using gD (gD 43B318) as the coating antigen. The antigen and antibody solutions were used at 50 µl per well. The antigen was diluted at a final concentration of 1 µg/ml in PBS and was adsorbed overnight at 4° C. to the wells of 96 wells microtiter plates (Maxisorb Immuno-plate, Nunc, Denmark). The plates were then incubated for 1 hr at 37° C. with PBS containing 1% bovine serum albumin and 0.1% Tween 20 (saturation buffer; 100 µl/well). Two-fold dilutions of sera (starting at 1/100 dilution) in the saturation buffer were added to the gD-coated plates and incubated for 1 hr 30 min at 37° C. The plates were washed four times with PBS 0.1% Tween 20 and biotin-conjugated anti-mouse IgG1, IgG2a, IgG2b or Ig (Amersham, UK) diluted 1/1000 in saturation buffer was added to each well and incubated for 1 hr 30 min at 37° C. After a washing step, streptavidin-biotinylated peroxydase complex (Amersham, UK) diluted 1/1000 in saturation buffer was added for an additional 30 min at 37° C. Plates were washed as above and incubated for 20 min with a solution of o-phenylenediamine (Sigma) 0.04% $H_2O_2$ 0.03% in 0.1% tween 20 0.05M citrate buffer pH 4.5. The reaction was stopped with $H_2SO_4$ 2N and read at 490/630 nm. ELISA titers were calculated from a reference by SoftmaxPro (using a four parameters equation) and expressed in EU/ml.

Anti-HBs Serology

The quantitation of anti-HBs antibody was performed by ELISA using HBs (Hep 286) as the coating antigen. Antigen and antibody solutions were used at 50 µl per well. The antigen was diluted at a final concentration of 1 µg/ml in PBS and was adsorbed overnight at 4° C. to the wells of 96 wells microtiter plates (Maxisorb Immuno-plate, Nunc, Denmark). The plates were then incubated for 1 hr at 37° C. with PBS containing 1% bovine serum albumin and 0.1% Tween 20 (saturation buffer). Two-fold dilutions of sera (starting at 1/100 dilution) in the saturation buffer were added to the HBs-coated plates and incubated for 1 hr 30 min at 37° C. The plates were washed four times with PBS 0.1% Tween 20 and biotin-conjugated anti-mouse Ig (Amersham, UK) diluted 1/1500 or IgG1, IgG2a, IgG2b (IMTECH, USA) diluted respectively at 1/4000, 1/8000, 1/4000 in saturation buffer were added to each well and incubated for 1 hr 30 min at 37° C. After a washing step, streptavidin-biotinylated peroxydase complex (Amersham, UK) diluted 1/1000 in saturation buffer was added for an additional 30 min at 37° C. Plates were washed as above and incubated for 20 min with a solution of o-phenylenediamine (Sigma) 0.04% $H_2O_2$ 0.03% in 0.1% tween 20 0.05M citrate buffer pH4.5. The reaction was stopped with $H_2SO_4$ 2N and read at 490/630 nm. ELISA titers were calculated from a reference by SoftmaxPro (using a four parameters equation) and expressed in EU/ml.

Cytokine Production

Two weeks after the second immunisation, mice were killed, spleens were removed aseptically and pooled. Cell suspensions were prepared in RPMI 1640 medium (GIBCO) containing 2 mM L-glutamine, antibiotics, $5 \times 10^{-5}$ M 2-mercaptoethanol, and 5% foetal calf serum. Cells were cultured at a final concentration of $5 \times 10^6$ cells/ml, in 1 ml per flat-bottomed 24 well-plates with different concentrations (10-1 µg/ml) of each of the Ag (VLPs, gD or HBs antigen). Supernatants were harvested 96 hrs later and frozen until tested for the presence of IFNγ and IL5 by ELISA.

IFNγ (Genzyme)

Quantitation of IFNγ was performed by ELISA using reagents from Genzyme. Samples and antibody solutions were used at 50 µl per well. 96-well microtiter plates (Maxisorb Immuno-plate, Nunc, Denmark) were coated overnight at 4° C. with 50 µl of hamster anti-mouse IFNγ diluted at 1.5 µg/ml in carbonate buffer pH 9.5. Plates were then incubated for 1 hr at 37° C. with 100 µl of PBS containing 1% bovine serum albumin and 0.1% Tween 20 (saturation buffer). Two-fold dilutions of supernatant from in vitro stimulation (starting at ½) in saturation buffer were added to the anti-IFNγ-coated plates and incubated for 1 hr 30 min at 37° C. The plates were washed 4 times with PBS Tween 0.1% (wash buffer) and biotin-conjugated goat anti-mouse IFNγ diluted in saturation buffer at a final concentration of 0.5 µg/ml was added to each well and incubated for 1 hr at 37° C. After a washing step, AMDEX conjugate (Amersham) diluted 1/10000 in saturation buffer was added for 30 min at 37° C. Plates were washed as above and incubated with 50 µl of TMB (Biorad) for 10 min. The reaction was stopped with $H_2SO_4$ 0.4N and read at 450/630 nm. Concentrations were calculated using a standard curve (mouse IFNγ standard) by SoftmaxPro (four parameters equation) and expressed in pg/ml.

IL5 (Pharmingen)

Quantitation of IL5 was performed by ELISA using reagents from Pharmingen. Samples and antibody solutions were used at 50 µl per well. 96-well microtiter plates (Maxisorb Immuno-plate, Nunc, Denmark) were coated overnight at 4° C. with 50 µl of rat anti-mouse IL5 diluted at 1 µg/ml in carbonate buffer pH 9.5. Plates were then incubated for 1 hr at 37° C. with 100 µl PBS containing 1% bovine serum albumin and 0.1% tween 20 (saturation buffer) .Two-fold dilutions of supernatant from in vitro stimulation (starting at ½) in saturation buffer were added to the anti-IL-5-coated plates and incubated for 1 hr 30 min at 37° C. The plates were washed 4 times with PBS Tween 0.1% (wash buffer) and biotin-conjugated rat anti-mouse IL5 diluted in saturation buffer at a final concentration of 1 µg/ml was added to each well and incubated for 1 hr at 37° C. After a washing step, AMDEX conjugate (Amersham) diluted 1/10000 in saturation buffer was added for 30 min at 37° C. Plates were washed as above and incubated with 50 µl of TMB (Biorad) for 15 min. The reaction was stopped with $H_2SO_4$ 0.4N and read at 450/630 nm. Concentrations were calculated using a standard curve (recombinant mouse IL-5) by SoftmaxPro (four parameters equation) and expressed in pg/ml.

Groups

Groups of 10 Balb/C mice were immunised intramuscularly with the following formulations:

TABLE 1

Groups and formulations

| GROUP | FORMULATION |
|---|---|
| A | VLP16 2 µg/VLP18 2 µg/gD 2 µg/3D-MPL 5 µg/Al(OH)$_3$ 50 µg |
| B | VLP16 2 µg/VLP18 2 µg/HBs 2 µg/gD 2 µg/3D-MPL 5 µg/Al(OH)$_3$ 40 µg/AlPO$_4$ 10 µg |
| C | gD 2 µg/3D-MPL 5 µg/Al(OH)$_3$ 50 µg |
| D | VLP16 2 µg/VLP18 2 µg/3D-MPL 5 µg/Al(OH)$_3$ 50 µg |
| E | HBs 2 µg/3D-MPL 5 µg/AlPO$_4$ 10 µg/Al(OH)$_3$ 40 µg |

Details of formulations are described above in Materials and Methods.

Results

1. Serology a) Anti-VLP16 Response:

Humoral responses (Ig) were measured by ELISA using VLP16 503-1 (20/12/99) as the coating antigen. Day 14 post II sera were analysed.

FIG. 1 shows anti-VLP16 Ig antibody responses measured on individual sera on day 14 post II.

The anti-VLP16 titers obtained after immunisation with the combination of VLPs, gD and HBs Ag (group B), were slightly lower than the one obtained with either the combination of VLPs and gD (group A) or the monovalent VLPs formulation (group D) (GMT respectively of 27578 versus 48105 EU/ml versus 44448 EU/ml). Before statistical analysis a T-Grubbs test was applied on each population for data exclusion. Two non-responder mice in groups A and D were eliminated for analysis.

The differences observed between the groups were shown as statistically not significant using the Student Newman Keuls Test.

b) Anti-VLP18 Response

Humoral responses (Ig) were measured by ELISA using VLP18 504-2 (25/10/99) as coating antigen. Day 14 post II sera were analysed.

FIG. 2 shows the anti-VLP18 Ig antibody response measured on individual sera on day 14 post II The anti-VLP18 titers obtained after immunisation with the combination of VLPs, gD and HBs Ag (group B), were in the same magnitude as the titers obtained with either the combination of VLPs and gD (group A) or the monovalent VLPs formulation (group D) (GMT respectively of 56078 versus 88786 EU/ml versus 76991 EU/ml)

Before statistical analysis a T-Grubbs test was applied on each population for data exclusion. Two non-responder mice in groups A and D were eliminated for analysis.

The differences observed were shown as statistically not significant using one-way analysis of variance test.

c) Anti-gD Response

Humoral responses (Ig and isotypes) were measured by ELISA using gD as coating antigen. Day 14 post II sera were analysed.

FIG. 3 shows the anti-gD antibody responses measured on individual sera at day 14 post II:

Regarding the anti-gD response, a slight decrease was observed in the GMT obtained with the VLPs/gD/HBs combination (group B) compared to gD alone (Group C) or VLPs/gD combination (Group A) (GMT respectively of 18631 versus 32675 versus 27058 EU/ml).

Before statistical analysis a T-Grubbs test was applied on each population for data exclusion. Two non-responder mice in group A were eliminated for analysis.

A one-way-analysis of variance was performed on anti-gD titers after log transformation of post II data. No statistically significant difference was observed between the three formulations.

The isotypic repartition analysed on pooled sera was as follows:

| | Isotypic repartition (%) | | |
|---|---|---|---|
| | IgG1 | IgG2a | IgG2b |
| Group A | 96 | 3 | 2 |
| Group B | 96 | 3 | 2 |
| Group C | 97 | 1 | 1 |

No difference was observed in isotypic profile induced by the three formulations: mainly IgG1 response (96–97% of IgG1) were induced in the 3 groups as reported in the table below.

d) Anti-HBs Response

Humoral responses (Ig and isotypes) were measured by ELISA using HBsAg (Hep286) as coating antigen. Day 14 post II sera were analysed.

FIG. 4 shows the anti-HBs antibody responses measured on individual sera on day 14 post II.

A slightly lower anti-HBs antibody response is observed in the combination group B containing the VLPs, gD and HBs antigens compared to HBs alone (group E) (GMT of 28996 EU/mi versus 20536 EU/ml).

A one-way-analysis of variance was performed on anti-HBs titers after log transformation of post II data. No statistically significant difference was observed between the group B (VLP/HBs/gD) versus the group E (HBs AS04) using Student Newman Keuls test.

The isotypic repartition analysed on pooled sera was as follows and showed no differences between the 2 groups with a proportion of IgG2a preserved in the combination vaccine.

| | Isotypic repartition (%) | | |
|---|---|---|---|
| | IgG1 | IgG2a | IgG2b |
| Group B | 54 | 24 | 21 |
| Group E | 56 | 23 | 21 |

2. Cell Mediated Immune Response

Cell-mediated immune responses (IFNγ/IL5 production) were evaluated at day 14 post II after in vitro restimulation of splenic cells with either VLPs, gD or HBs antigens. For each group of mice, pools of 5 organs were constituted. The experimental procedure is fully described in Material and Methods.

3. Cytokine Production a) In Vitro Restimulation with VLP16 and VLP18

FIG. 5 shows the cytokine production monitored in splenic cells after 96 h in vitro restimulation with VLP16.

FIG. 6 shows the cytokine production monitored in splenic cells after 96 h in vitro restimulation with VLP18.

No clear dose range effect has been observed using 10 µg and 1 µg Ag dose for restimulation with either VLP antigens on both cytokine production.

A clear TH1 profile was observed with all formulations.

TABLE 2

IFN-γ/IL-5 ratio after in vitro restimulation with VLP16 and VLP18.

| Ratio IFN/IL-5 | Group A | Group B | Group D |
|---|---|---|---|
| VLP16 10 µg/ml | 5.2 | 8.9 | 11.8 |
| VLP16 1 µg/ml | 15.1 | 14.3 | 16.5 |
| VLP18 10 µg/ml | 19.6 | 11.1 | 16.1 |
| VLP18 1 µg/ml | 23.2 | 14.3 | 18.2 | b) In Vitro Restimulation with gD

FIG. 7 shows the cytokine production monitored in splenic cells after 96 h in vitro restimulation with gD antigen.

No clear dose range effect was observed when comparing the 10 and 1 µg Ag dose for restimulation The IFN-γ is produced in much higher concentration as compared to IL-5 (Table 3) indicating a clear TH-1 profile of the immune response in all groups evaluated (monovalent versus combination).

TABLE 3

IFN-γ/IL-5 ratio after in vitro restimulation with gD.

| Ratio IFN/IL-5 | Group A | Group B | Group C |
|---|---|---|---|
| gD 10 µg/ml | 6.2 | 7.2 | 3.1 |
| gD 1 µg/ml | 6.2 | 11.2 | 2.3 | c) In Vitro Restimulation with HBs

FIG. 8 shows the cytokine production monitored in splenic cells after 96 h in vitro restimulation with HBs.

A significant level of IFN-γ but no IL5 production was observed for group B. As shown in Table 2 higher production of IFN-γ was observed in group E as compared to group B. However high background value of IFN-γ was observed in the group E (HBs monovalent) for the control with no antigen for restimulation. A very high IFN-γ/IL-5 ratio was observed with the monovalent vaccine indicating that a strong TH1 response is induced. Similarly, a high IFN-γ/IL-5 ratio was measured with the combined vaccine confirming the ability of this formulation to also induce a TH-1 response.

TABLE 4

IFN-γ/IL-5 ratio after in vitro restimulation with HBs.

| Ratio IFN/IL-5 | Group B | Group E |
|---|---|---|
| HBs 10 µg/ml | 15.8 | 65.3 |
| HBs 1 µg/ml | 7.6 | 67.6 |

CONCLUSION

The effect of the combination of VLPs/gD or VLPs/gD/HBs Ag formulated in AS04 on the immunogenicity was evaluated in Balb/C mice:

Regarding the serological analysis, no interference of the Ag combination was observed on anti-VLPs, anti-gD and anti-HBs serology.

The combination of VLPs and gD or VLPs, gD and HBs antigens did not interfere with the isotypic profile of the antibody response displayed by the gD and HBs monovalent vaccines.

In the cytokines evaluation, the TH-1 profile (IFN-γ/IL-5 ratio) observed with each monovalent vaccines was confirmed with the combination vaccine groups.

What is claimed is:

1. A vaccine comprising an HPV 16 L1 VLP, an HPV 18 L1 VLP, aluminium hydroxide and 3D MPL.
2. A vaccine according to claim 1 wherein the VLPs are formulated using pre-adsorbed purified bulks of antigen or 3D MPL on aluminium hydroxide.
3. A vaccine according to claim 2 wherein the HPV 16 L1 VLP and HPV 18 L1 VLP purified bulks are added to aluminium hydroxide to obtain a ratio of 2 µg VLP/10 µg aluminium hydroxide.
4. The vaccine of claim 1 consisting of an HPV 16 L1 VLP, an HPV 18 L1 VLP, aluminium hydroxide and 3D MPL.
5. An HPV 16 L1 VLP formulated with alum/3D-MPL using pre-adsorbed purified bulk of antigen or 3D MPL on aluminium hydroxide or aluminium phosphate.
6. An HPV 18 L1 VLP formulated with alum/3D-MPL using pre-adsorbed purified bulk of antigen or 3D MPL on aluminium hydroxide or aluminium phosphate.

* * * * *

UNITED STATES PATENT AND TRADEMARK OFFICE
CERTIFICATE OF CORRECTION

| | | |
|---|---|---|
| PATENT NO. | : 7,101,560 B2 | Page 1 of 1 |
| APPLICATION NO. | : 10/734857 | |
| DATED | : September 5, 2006 | |
| INVENTOR(S) | : Moncef Mohamed Slaoui | |

It is certified that error appears in the above-identified patent and that said Letters Patent is hereby corrected as shown below:

On Title page, (75) Inventor: Martine Anne Wettendorff, should be: Moncef Mohamed Slaoui Signed and Sealed this Twenty-eighth Day of November, 2006

JON W. DUDAS
*Director of the United States Patent and Trademark Office*